United States Patent
Purohit et al.

(10) Patent No.: US 12,290,280 B2
(45) Date of Patent: May 6, 2025

(54) SYSTEM, DEVICE AND METHOD COMBINING BIOABSORBABLE FOAM WITH VACUUM TECHNOLOGY FOR NEOPLASTIC CYSTS

(71) Applicant: Boston Scientific Medical Device Limited, Galway (IE)

(72) Inventors: Hitendra Purohit, Vadodara / Guj (IN); Agrim Mishra, New Delhi / Delhi (IN); Deepak K. Sharma, Muzaffarnafar / Up (IN); Subodh Morey, Ponda / Goa (IN); Nabarun Bhowmick, Kolkata/ West Bengal (IN)

(73) Assignee: Boston Scientific Medical Device Limited, Galway (IE)

( * ) Notice: Subject to any disclaimer, the term of this patent is extended or adjusted under 35 U.S.C. 154(b) by 319 days.

(21) Appl. No.: 17/167,526

(22) Filed: Feb. 4, 2021

(65) Prior Publication Data
US 2021/0236160 A1 Aug. 5, 2021

Related U.S. Application Data

(60) Provisional application No. 62/984,395, filed on Mar. 3, 2020, provisional application No. 62/970,387, filed on Feb. 5, 2020.

(51) Int. Cl.
*A61B 17/34* (2006.01)
*A61B 17/00* (2006.01)
(Continued)

(52) U.S. Cl.
CPC .... *A61B 17/3415* (2013.01); *A61B 17/00234* (2013.01); *A61B 17/3403* (2013.01);
(Continued)

(58) Field of Classification Search
CPC .......... A61B 17/3415; A61B 17/00234; A61B 17/3403; A61B 17/3417; A61B 17/3468;
(Continued)

(56) References Cited

U.S. PATENT DOCUMENTS

| 2002/0052653 A1 | 5/2002 | Durgin |
| 2006/0173296 A1* | 8/2006 | Miller .................... A61B 90/39 |
| | | 600/431 |

(Continued)

FOREIGN PATENT DOCUMENTS

| CN | 110167529 A | 8/2019 |
| EP | 111618 A2 | 6/1984 |

(Continued)

OTHER PUBLICATIONS

International Search Report and Written Opinion for the International Patent Application No. PCT/IB2021/050924, mailed Apr. 12, 2021, 13 pages.

(Continued)

*Primary Examiner* — Nathan R Price
*Assistant Examiner* — Fatimata Sahra Diop
(74) *Attorney, Agent, or Firm* — Bookoff McAndrews, PLLC

(57) ABSTRACT

A device for draining cysts includes a catheter system configured to deploy an absorbent material, including but not limited to a foam, into a cyst. The absorbent material advantageously absorbs fluid contained within the cyst, for example fluid that may remain following aspiration, reducing the potential for cyst recurrence. In various embodiments, the absorbent material may be bioabsorbable, radiolucent, echogenic, drug eluting, or a combination thereof. In some embodiments the device may further include or be coupled to a vacuum source which applies negative pressure (Continued)

to the cyst during foam delivery, thereby reduce the overall size and/or profile of the cyst.

18 Claims, 7 Drawing Sheets

(51) Int. Cl.
*A61M 25/00* (2006.01)
*A61M 37/00* (2006.01)
*A61M 25/06* (2006.01)

(52) U.S. Cl.
CPC ........ *A61B 17/3417* (2013.01); *A61M 25/003* (2013.01); *A61M 37/0069* (2013.01); *A61B 2017/00004* (2013.01); *A61B 2017/00296* (2013.01); *A61B 2017/00893* (2013.01); *A61B 2017/3405* (2013.01); *A61B 2017/345* (2013.01); *A61B 2017/3454* (2013.01); *A61B 17/3468* (2013.01); *A61B 2217/005* (2013.01); *A61M 2025/0057* (2013.01); *A61M 2025/0681* (2013.01)

(58) Field of Classification Search
CPC ........... A61B 2017/00004; A61B 2017/00296; A61B 2017/00893; A61B 2017/3405; A61B 2017/345; A61B 2017/3454; A61B 2217/005; A61B 17/3478; A61B 17/2202; A61B 90/39; A61B 2017/3413; A61B 2090/0815; A61M 25/003; A61M 37/0069; A61M 2025/0057; A61M 2025/0681; A61M 1/916; Y10S 604/904; A61F 13/15; A61F 13/00068
See application file for complete search history.

(56) References Cited

U.S. PATENT DOCUMENTS

| | | |
|---|---|---|
| 2014/0276514 A1 | 9/2014 | Simon |
| 2017/0181764 A1 | 6/2017 | Braun et al. |
| 2018/0126126 A1* | 5/2018 | Ornelas Vargas ........................... A61M 25/09041 |
| 2022/0071732 A1* | 3/2022 | Rebellino .......... A61B 10/0233 |

FOREIGN PATENT DOCUMENTS

| | | | |
|---|---|---|---|
| EP | 1114618 A2 * | 7/2001 | ....... A61B 17/00234 |
| WO | 2009100106 A1 | 8/2009 | |

OTHER PUBLICATIONS

Office Action in Chinese Application No. 202180026160.1, dated Jan. 23, 2025 (16 pages).

* cited by examiner

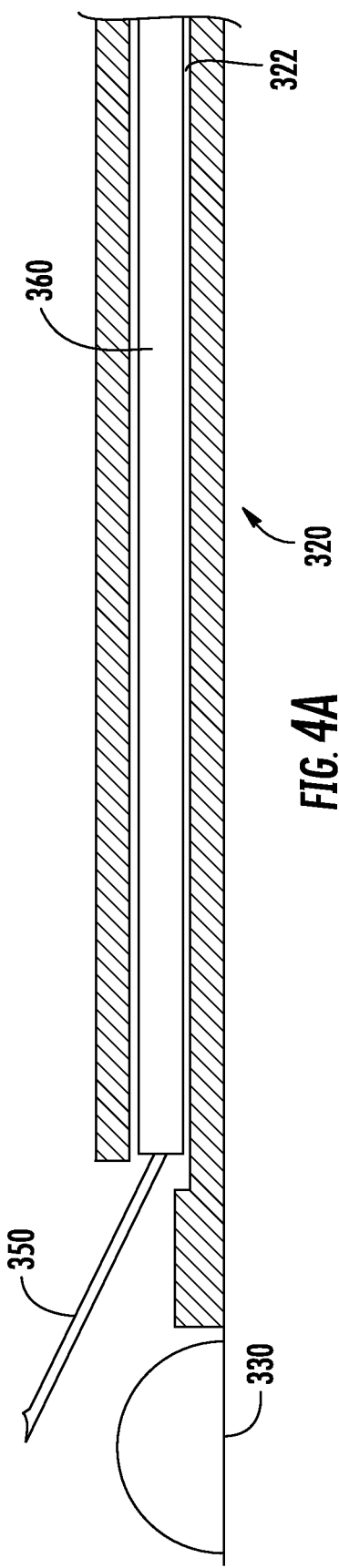
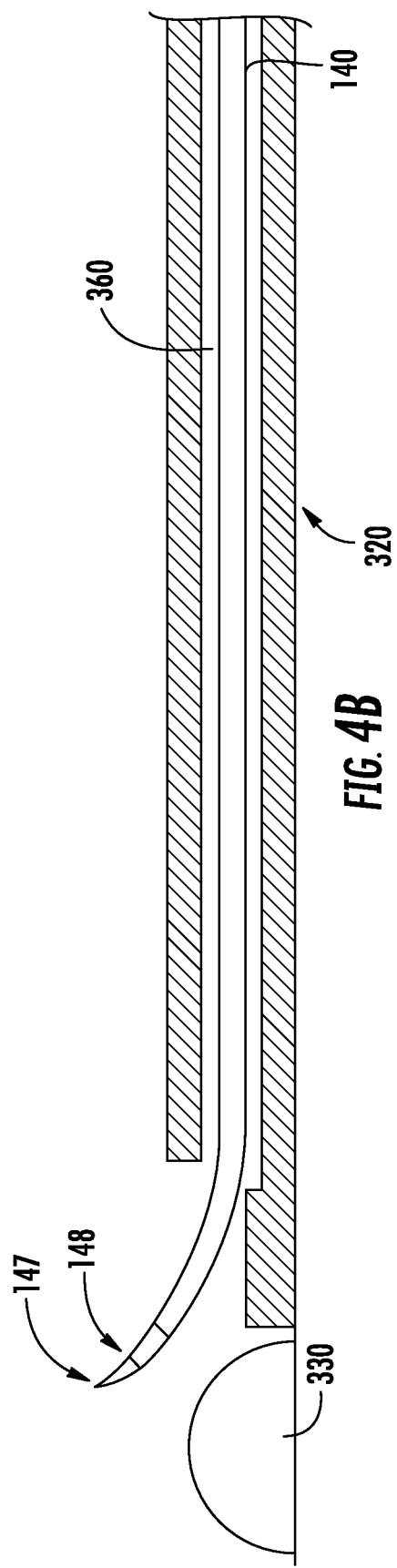

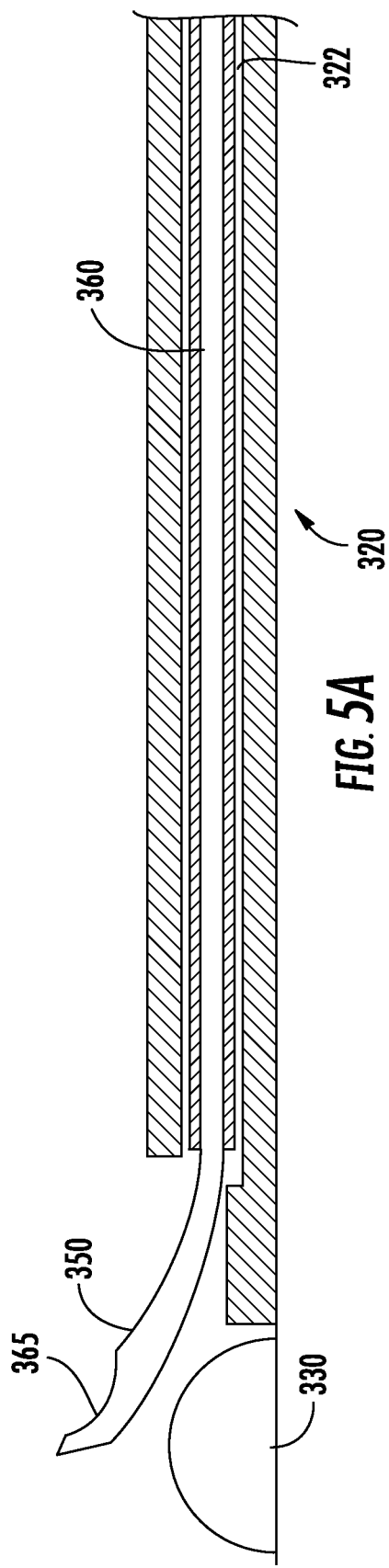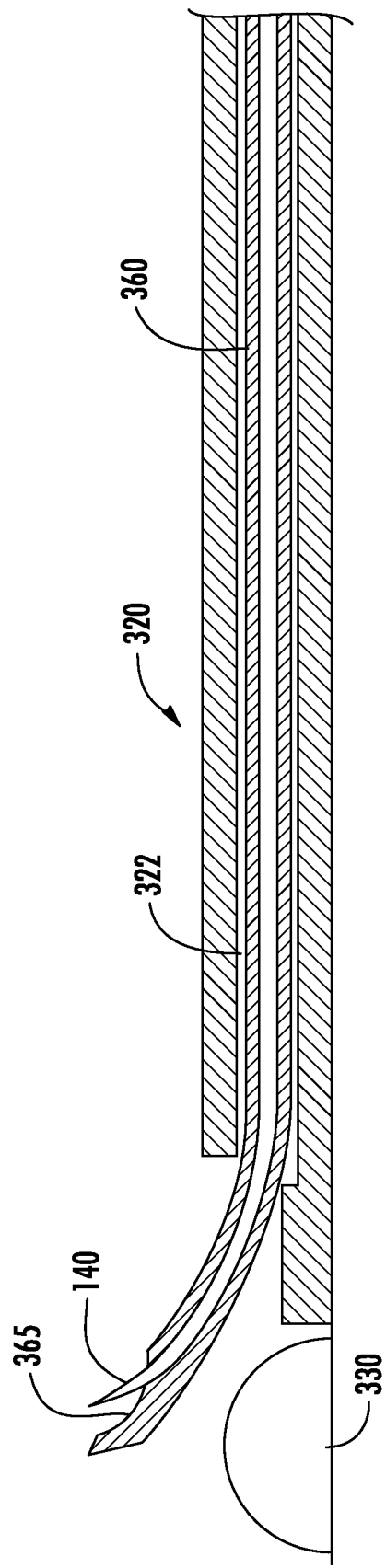

SYSTEM, DEVICE AND METHOD COMBINING BIOABSORBABLE FOAM WITH VACUUM TECHNOLOGY FOR NEOPLASTIC CYSTS

CROSS-REFERENCE TO RELATED APPLICATIONS

The present application claims the benefit of priority under 35 U.S.C. § 119 to U.S. Provisional Patent Application No. 62/970,387 filed Feb. 5, 2020, and to U.S. Provisional Patent Application No. 62/984,395 filed Mar. 3, 2020, which applications are incorporated herein by reference in their entireties for all purposes.

FIELD

The present disclosure pertains to medical devices generally and in particular to medical devices such as for cyst management.

BACKGROUND

Pancreatic cancer is the third-leading cause of cancer death in the United States. Approximately twenty to thirty percent of pancreatic cancers originate from mucinous type pancreatic cysts, which are found in two percent of Americans and become increasingly prevalent with age.

Because cyst disruption can accelerate the spread of the disease, commonly cysts are monitored using non-invasive imaging techniques, such as Computed Tomography (CT) and Magnetic Resonance Imaging (MRI) to categorize and monitor cyst development. Imaging may be repeated on a regular basis (such as every six months). While imaging is less invasive, it provides an inexact diagnosis which may increase patient anxiety and delay diagnosis.

Endoscopic ultrasound (EUS) is a procedure used to diagnose and evaluate pancreatic cysts. In this procedure, an endoscopic ultrasound is advanced through a patient's mouth into the stomach and duodenum, from where it can image the pancreas. A needle may be used to aspirate fluid from the cyst for biopsy purposes. While such techniques are effective for diagnosis purposes, a high recurrence of cysts, particularly in prior, aspirated cyst locations, is common and may increase the frequency and number of biopsy procedures. It would be desirable to identify a less invasive device and method for cyst categorization, diagnosis, and treatment with improved accuracy.

SUMMARY

According to one aspect, a device (such as, but not limited to, a device for draining cysts) includes a catheter having a proximal end, a distal end, a lumen extending from the proximal end to the distal end; and a sheath disposed about the distal end of the catheter, wherein a distal tip of the sheath extends beyond the distal end of the catheter to form a chamber distally of the distal end of the catheter. The device includes an absorbent material disposed within the chamber of the sheath, a handle coupled to the sheath and including a release or deployment mechanism ("release" mechanism herein for the sake of convenience and without intent to limit) configured and positioned to release the absorbent material from the chamber, and a vacuum passage disposed for application of a proximal suction force through the catheter lumen.

In various embodiments, the handle may include the vacuum source, or the handle may be coupled to the vacuum source. The handle may include a housing having a bore extending from a proximal opening of the housing to a distal inlet of the housing, where the proximal end of the catheter is fluidly coupled to the distal inlet of the housing. In one embodiment, the vacuum source includes a plunger rod translatably disposed within the bore, the plunger rod including a plunger translatable within the bore, where proximal advancement of the plunger rod and the plunger through the bore increases a pressure within the housing and the lumen of the catheter to generate the proximal suction force. In some embodiments, the release mechanism includes one of a knob, a switch, a thumbwheel, a button, a dial, or a combination thereof. In various embodiments the absorbent material includes foam. The foam may be bioabsorbable, formed from a radiolucent or echogenic material, be a drug eluting foam, or a combination thereof. In one embodiment, the catheter of the device may be shaped and configured for translation through a working channel of an endoscope. In one embodiment the catheter may be shaped and configured for translation through a needle lumen of a needle catheter.

According to another aspect, a catheter system includes a catheter having a proximal end, a distal end, and a catheter lumen extending from the proximal end to the distal end; and a sheath disposed about the distal end of the catheter, the sheath having a distal tip that extends distally beyond the distal end of the catheter to form a chamber distally of the distal end of the catheter. The catheter system includes an absorbent material having a compressed configuration sized to fit within the chamber of the sheath, and an expanded configuration larger than the compressed configuration, the absorbent material including a radiolucent material, an echogenic material, a drug eluting material, a bioabsorbable material, or a combination thereof. The catheter system includes a handle coupled to the sheath and including a release mechanism configured and positioned to release the absorbent material from the chamber, and a vacuum passage disposed for application of a proximal suction force through the catheter lumen.

In various embodiments, the release mechanism configured and positioned to release the absorbent material may include a knob, a switch, a thumbwheel, a button, a dial, or a combination thereof. The catheter system may further include a housing having a bore extending from a proximal opening of the housing to a distal inlet of the housing, where the distal inlet is fluidly coupled to the proximal end of the catheter. The vacuum source may include a plunger rod translatably disposed within the bore, the plunger rod including a plunger translatable within the bore, where proximal advancement of the plunger rod and the plunger through the bore decreases a pressure within the housing and the catheter lumen to generate the proximal suction force. The catheter may be shaped and configured for translation through a working channel of an endoscope, a lumen of a needle catheter, or both.

According to a further aspect, a method includes advancing a catheter through a body lumen into a cyst, the catheter having a proximal end, a distal end, and a catheter lumen extending therethrough, the catheter including an elongate body disposed within a sheath, the sheath extending distally from the distal end of the catheter to form a chamber having an absorbent material stored therein. The method includes releasing the absorbent material from the chamber of the sheath into the cyst, applying a proximal suction force through the catheter lumen to reduce the cyst and to compress the absorbent material within the cyst, and removing the catheter from the cyst and the body lumen.

In various embodiments, the catheter includes a proximal handle including a housing having a bore extending from a proximal opening of the housing to a distal inlet of the housing, where the distal inlet of the housing is fluidly coupled to the proximal end of the catheter, a plunger rod translatably disposed within the bore, the plunger rod including a plunger translatable within the bore. The method includes applying the proximal suction force including proximally withdrawing the plunger rod and the plunger through the bore to generate the proximal suction force through the distal inlet and the catheter. In some embodiments, the method includes advancing the catheter through the working channel of an endoscope to the cyst. In some embodiments, the method includes advancing the catheter through a needle lumen of a needle catheter to the cyst. In some embodiments, the method includes draining the cyst using the needle catheter prior to inserting and advancing the catheter through the needle catheter, and where applying the proximal suction force through the catheter lumen uses a needle aspiration suction force.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIGS. 4A and 4B are cross sectional views illustrating one embodiment of a method of use in a catheter system such as that described with regard to FIG. 1A with an endoscope such as that of FIG. 2;

FIGS. 5A and 5B are cross-sectional views illustrating one embodiment of a method of use in a catheter system such as that described with regard to FIG. 1A with an endoscope such as that of FIG. 2;

DETAILED DESCRIPTION

A device such as for managing cysts includes a catheter system shaped and configured to deploy an absorbent material, including but not limited to a foam, such as into a cyst. The absorbent material advantageously absorbs fluid (e.g., contained within a cyst), for example fluid that may remain following aspiration, reducing the potential for cyst recurrence. In various embodiments, the absorbent material may be bioabsorbable, radiolucent, echogenic, drug eluting, or a combination thereof.

In one embodiment, the device may further include or be coupled to a vacuum source which applies negative pressure to the cyst during and/or following foam delivery for drainage of the cyst, thereby reducing the overall size and/or profile of the cyst. Reducing the overall profile of the cyst may decrease the potential for cyst recurrence. In addition, reducing the overall profile may increase contact between the foam and the cyst sidewalls. In embodiments where the foam is coated with or otherwise incorporates drugs for localized therapy of the cyst, applying such vacuum pressure may increase treatment efficacy.

Various embodiments of such a device and method of cyst management will now be described. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

As used herein, the term "distal" refers to the end farthest away from the medical professional when introducing a medical device into a patient, while the term "proximal" refers to the end closest to the medical professional when introducing a medical device into a patient. A central axis means, with respect to an opening, a line that bisects a center point of the opening, extending longitudinally along the length of the opening when the opening comprises, for example, a tubular frame, a strut, or a bore.

Figure 1:
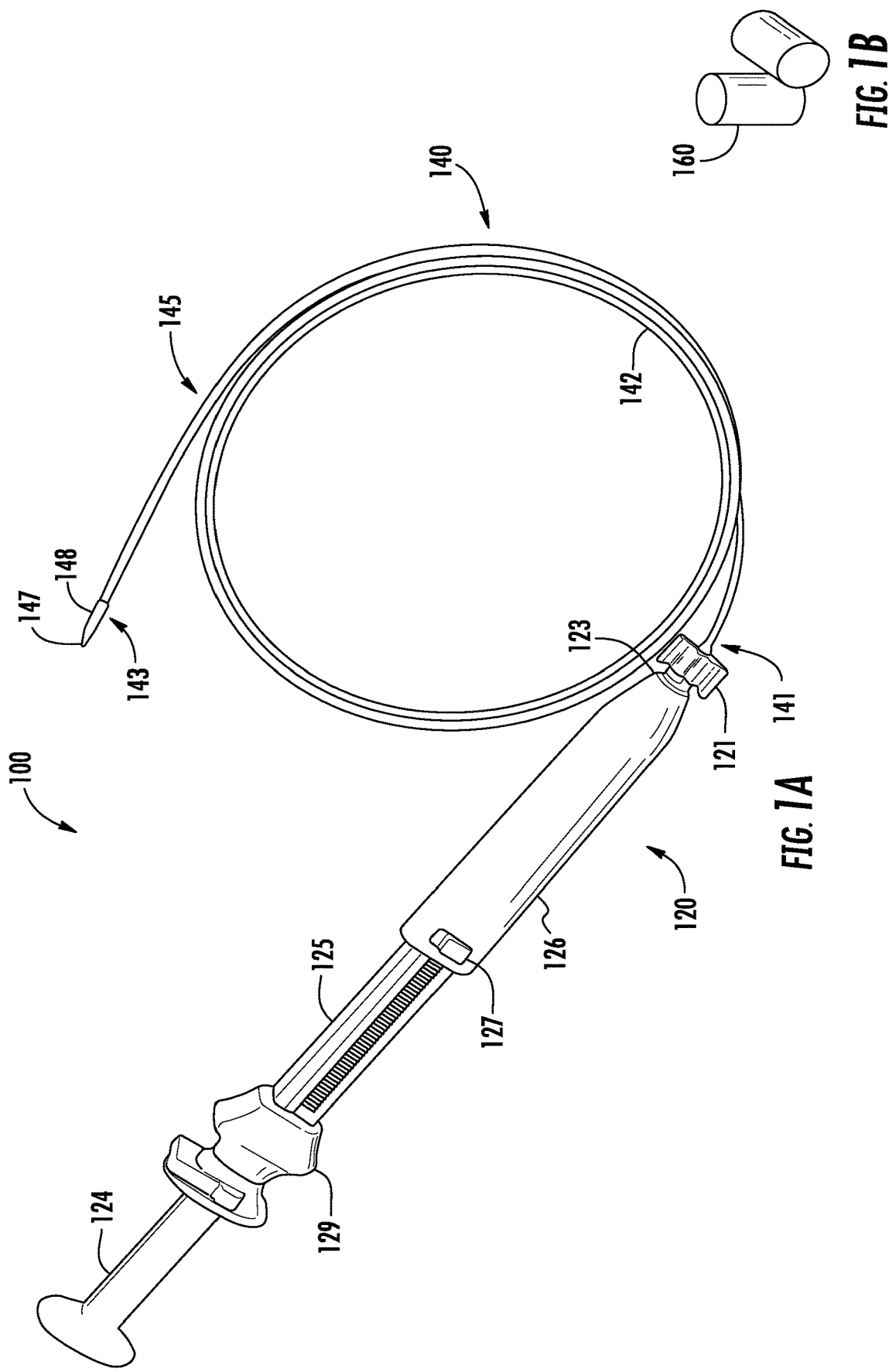
FIGS. 1A and 1B illustrate one embodiment of a catheter system for deploying an expandable material.

FIG. 1A illustrates an example of a catheter system 100 including a handle 120 coupled to a catheter 140. The catheter 140, in one embodiment, comprises an elongate body 142 having a proximal end 141 releasably coupled to the handle 120 (for example, screwed on via knob 121) and a distal end 143. In one embodiment, the catheter may comprise a composite of layers of thermoplastic elastomer (TPE). Alternatively, nylon, polyurethanes, polyester, silicone, or other similar materials may be used to provide thin walls that may be extruded and layered over braided wires or coils for tensile and hoop strength, although the disclosed system is not limited to any particular material composition.

According to one embodiment, the catheter system is shaped and configured for management of pancreatic cysts, although the disclosure is not limited to use in the pancreas, and it is appreciated that the principles disclosed herein may be extended by one of skill in the art to cyst management throughout a body.

However, for embodiments wherein the catheter is shaped and configured for pancreatic cyst management, the length of the catheter 140 may be selected to enable the catheter to be transluminally navigated through the gastrointestinal tract to the pancreas. For example, the length of the catheter may range from at least about 1300 millimeters (mm) to about 1600 mm, such as between about 1300 mm and 1500 mm, or between about 1400 mm and 1600 mm or the like.

In one embodiment, the catheter 140 may comprise a sheath 145, disposed over the elongate body of the catheter 140. Similar to the elongate body, the sheath may be comprised of a thermoplastic elastomer, nylon, polyurethane, polyester, silicone, or other similar materials. In one embodiment, the sheath 145 may have a distal end 147 that extends past the distal end 143 of the elongate body 142, forming a chamber inside the distal end 147 of the sheath, wherein an absorbent material (such as foam) may be disposed for delivery to a cyst treatment site. In some embodiments, the distal end 147 may include one or more echogenic features 148, facilitating visualization of the distal end 147 during ultrasound.

Outer diameters of the elongate body 142 and/or sheath 145 are selected to enable the catheter to be advanced freely within a working channel of an endoscope. For example, in various embodiments the outer diameter of the elongate body 142 and/or sheath 145 may be at least about 1.5 mm and at most about 3.5 mm, such to fit and be extendible within an endoscope working channel (for example, a working channel having a 3.8 mm diameter) although the disclosure is not so limited.

In some embodiments, the sheath 145 and elongate body 142 may be translatably disposed relative to each other to enable release of the foam from the distal end 147 of the sheath 145. For example, in some embodiments, the sheath may be shaped and configured to be withdrawn proximally of the distal end 143 of the elongate body 142 of the catheter 140, or the elongate body 142 may be disposed to move proximally within the sheath 145.

In other embodiments, the sheath 145 and elongate body 142 may be fixedly disposed relative to each other, and the elongate body may comprise a suitable release mechanism (e.g., a push rod or the like) configured and positioned to release and/or expel and/or deploy (hereinafter "release" for the sake of convenience, without intent to limit) the sheathed foam from the distal end 147 of the sheath. Various embodiments of release mechanisms known to those of ordinary skill in the art as configured and positioned to release a material, such as the absorbable material from the distal end 147 of the sheath 145, at a desired site are considered within the scope of this disclosure. For example, any of the following release mechanisms may be used: a pneumatic-assisted mechanism to release foam/powder/gel; a mechanical structure (e.g., screw mechanism, plunger (push) mechanism etc.) to release foam/powder/gel; a release foam (by changing state of foam/powder/gel).

In one embodiment, a lumen 144 (FIG. 2) extends from the proximal end 141 of the elongate body 142 of the catheter 140 through the distal end 147 of the sheath. The lumen 144 provides a fluid flow pathway between the distal end 147 and a vacuum source associated with the handle 120, enabling proximal fluid suction through the catheter 140 during a cyst management process as disclosed below.

The handle 120 includes a housing 126 having a bore 250 (FIG. 2) extending therethrough. In one embodiment, a vacuum cylinder 125 is adjustably disposed within the proximal portion of the handle housing bore and a distal inlet port 123 is disposed at a distal end of the bore of the housing 126. In one embodiment, the housing 126 may include a tab lock 127 that may be used to control an adjustment height, and concomitantly an available vacuum force, provided by the vacuum cylinder 125. The distal inlet port 123 fluidly couples the lumen 144 of the catheter 140 to the bore 250 of the housing 126.

In one embodiment, a plunger rod 124 is translatably disposed within the vacuum cylinder 125, wherein the plunger rod 124 includes a distal plunger 224 that seals the proximal end of the bore against air inflow from outside the housing 126. As a result, proximal translation of the plunger rod 124 within the vacuum cylinder 125 creates a negative pressure within the bore of the housing 126, providing a proximal vacuum/suction force through the distal inlet 123 of the housing that draws fluid (e.g., gas and/or liquid) through the lumen 144 of the catheter 140.

In some embodiments, the handle 120 may also comprise release mechanisms configured and positioned to control delivery of the absorbent material to the cyst. For example, a dial 129 is shown disposed about the vacuum cylinder 125 of the handle 120. In one embodiment, rotation of the dial may control a release mechanism internal to the handle/catheter, that is configured and positioned to release the absorbent material from the distal end 147 of the catheter sheath 145. It is appreciated that any of a variety of release mechanisms may be used to manage the release of the absorbent material, and other release mechanisms, such as switches, knobs, buttons, thumbwheels, and the like are considered to be within the scope of this disclosure.

FIG. 1B illustrates one embodiment of an absorbent material 160 that may be disposed within the chamber at the distal end 147 of the sheath 145 and used as disclosed herein. In one embodiment, the absorbent material 160 may comprise a foam or gel or powder or similar material having the ability to absorb and retain biological fluid from the cyst, including but not limited to blood, mucus, and other bodily fluids. The foam may be an open cell foam for promoting drainage. According to one aspect, it is appreciated that deploying foam into the cyst to absorb excess fluids may reduce the recurrence of a cyst in that location. Examples of foams that may be suitable for such purpose include those having hemostatic properties, such as those formed from of porcine gelatin (e.g. the GelForm™ Sponge, manufactured by Pharmacia, of Kalamazoo, Mich., or Surgifoam™ Sponge, manufactured by Ethicon, of Somerville, N.J.), those comprised of bovine collagen (e.g. Ultrafoam™, manufactured by Integra, of Plainsboro, N.J., Helistat, manufactured by Ethicon/J&J of Somerville, N.J.), those composed of oxidized regenerated cellulose (ORC) (e.g., Surgicel Oxycel, manufactured by Ethicon/J&J) and the like or a combination thereof. Although the absorbent material 160 of FIG. 1B is shown having a generally cylinder shape, the present disclosure is not limited to a foam having any particular shape and/or size. It is appreciated that the amount of foam delivered to a cyst is dependent upon the size of the cyst cavity, and it is anticipated that the amount of foam disposed within the distal end 147 of the sheath 145 may store foam sufficient to treat multiple cysts. In various embodiments foam may be stored in a compressed form having a smaller volume than in a delivered form, which may be an expanded form, when the foam is outside of the sheath 145. In various embodiments, foam may take on substantially the same volume, shape, and/or form within the sheath 145 and when delivered outside of the sheath 145. By way of example, sufficient foam may be stored to treat more than one cyst, or a cyst requiring a foam larger than the foam provided. The foam may be provided in one or more cartridges and deployed depending on cyst size and/or the number of cysts. It will be appreciated that the foam need not be stored in the catheter. Instead (or in addition) the foam can be loaded through the handle 120 (such as by syringe) or through the distal end 143 of the catheter 140.

In some embodiments, the foam may comprise additional characteristics, in addition to properties of absorption. For example, in one embodiment, the foam may be a soft, resilient hemostatic bio foam capable of conforming to the cyst cavity and transitioning to a porous gel or other substance that may be absorbed by the body over time. In some embodiments, the foam may be coated by, or otherwise incorporate, therapeutic agents that accelerate healing of the cyst, and/or provide localized treatment, including cancer treatment, such as any therapeutic agents having properties to delay generation of fluid or to delay conversion of a cyst to malignant tissue, or any drug or drugs (known or to be developed) having healing properties. In some embodiments, the foam may be marked with or formed from substances increasing visibility of the treated cyst cavity during subsequent foam placement and subsequent imaging, for example, including radiolucent or echogenic markers or the like.

Figure 2:
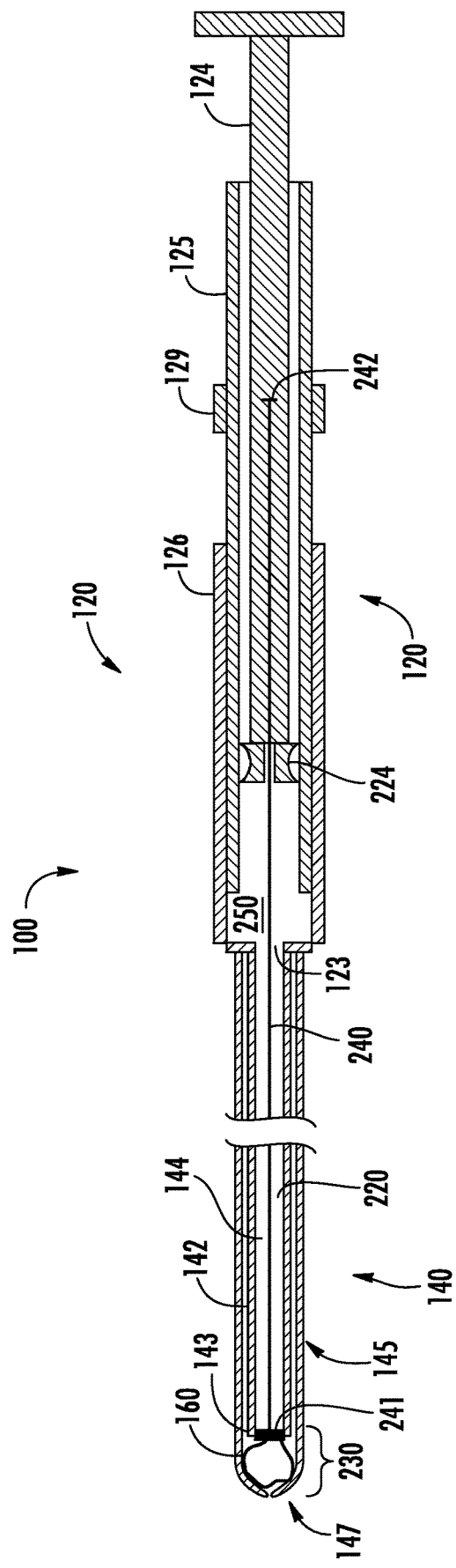
FIG. 2 is a cross-sectional view of the catheter system of FIG. 1A.

FIG. 2 is a cross-sectional view of the catheter system 100, showing a distal portion of catheter 140, and the handle 120. In FIG. 2, the foam 160 is visible within the distal end 147 of the catheter 140, disposed within a chamber 230 extending between the distal end 143 of the elongate body 142 of the catheter 140 and the distal end 147 of the sheath 145. A push rod 240 is positioned with a distal end 241 thereof adjacent to the chamber 230, and extends axially within the lumen 220 of the elongate body 142, from adjacent the chamber 230, through the distal inlet 123 of the handle housing 126 and into the housing 126 to a proximal end 242 of the push rod 240 positioned adjacent the release mechanism (e.g., dial) 129. Distal advancement of the push rod 240 by actuation of release mechanism 129 expels the foam 160 through the distal end 147 of the sheath 145.

An example of a vacuum source in the form of a plunger rod and plunger is illustrated in FIG. 2. A vacuum cylinder 125 is shown disposed within the bore 250 of the housing 126 and a plunger rod 124 is shown axially disposed within the vacuum cylinder 125. A plunger 224, disposed on the distal end of the plunger rod 124, may be formed of rubber or other material that enables the plunger rod 124 to move axially within the vacuum cylinder 125 without allowing external airflow into the bore 250. In various embodiments, a lumen (e.g., lumen 144 of FIG. 2) may be in fluid communication with a vacuum source (e.g., at a proximal end of the system 100).

Figure 3:
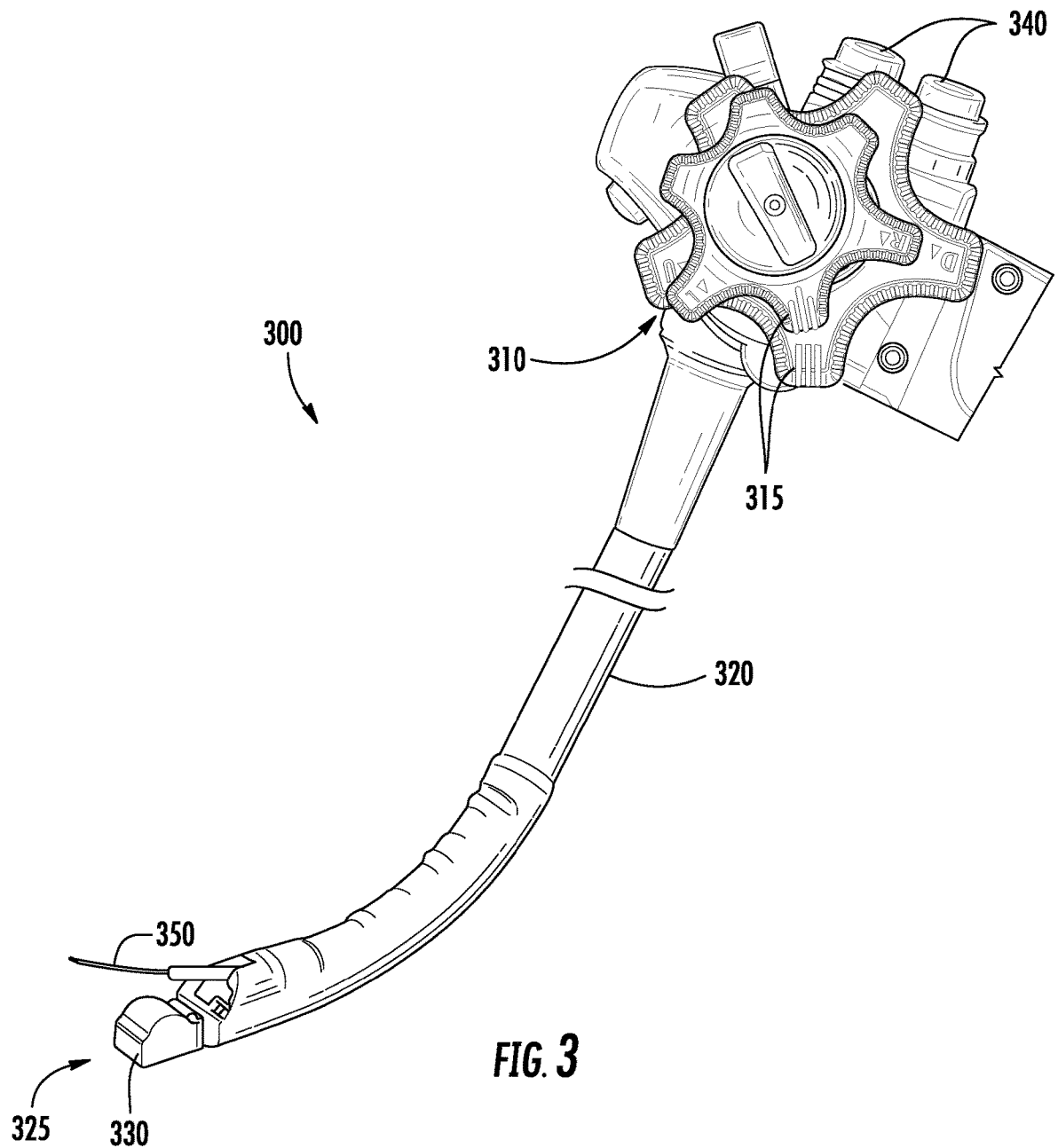
FIG. 3 illustrates one embodiment of an ultrasound endoscope including a working channel though which the catheter system of FIG. 1A may be deployed as disclosed herein.

According to one aspect, the catheter system 100 may be used as part of an Endoscopic Ultrasound (EUS) procedure for pancreatic cyst management. FIG. 3 illustrates one embodiment of an ultrasound endoscope 300 including a handle 310 and a steerable catheter 320 having an ultrasound transducer 330 disposed at its distal end. Various working channels may be disposed within the catheter 320, and instruments may access the working channels using one or more of the ports 340 disposed within the handle. Dials 315 of the handle 310 may be used to navigate a distal end 325 of the catheter 320 to a treatment site, e.g., to a cyst. FIG. 3 illustrates an aspiration needle 350, that has been disposed through a working channel of the endoscope 300 and deployed to aspirate fluid from a cyst.

FIGS. 4A and 4B are cross-sectional illustrations of a distal end of the endoscope 300, during a procedure, for example during cyst management. In FIG. 4A, an aspiration needle system 360, including a distal aspiration needle 350, has been forwarded distally through the working channel 322 of the catheter 320 of the endoscope. The needle 350 extends distally adjacent to the ultrasound transducer 330, enabling visualization of the aspiration procedure.

Following aspiration, the aspiration needle system 360 may be withdrawn from the working channel 322 while the endoscope is kept in position, and, as shown in FIG. 4B, the catheter 140 of the catheter system 100 may be advanced through the working channel 322 of the steerable catheter 320 to the aspirated cyst. Visualization of the distal end 147 of the catheter 140 is facilitated using the echogenic markers 148, which may be visualized using the ultrasound transducer 330.

FIGS. 5A and 5B are cross-sectional illustrations of a distal end of the endoscope 300, for example during another embodiment of a procedure such as cyst management. As in FIG. 4A, in FIG. 5A an aspiration needle system 360, including a distal aspiration needle 350 has been forwarded down the working channel 322 of the catheter 320 of the endoscope 300. The needle 350 extends distally adjacent to the ultrasound transducer 330, enabling visualization of the aspiration procedure. In FIG. 5A, the needle lumen 365, defining the aspiration path, is visible.

In FIG. 5B, following aspiration, the aspiration needle system 360 remains in place in the working channel 322, and the catheter 140 of the catheter system 100 may be advanced through the needle lumen 365 of the needle system 360 to the aspirated cyst. Accordingly, the catheter system may be advanced towards a cyst, and visualized, using a variety of available paths within the ultrasound endoscope.

FIGS. 6A-6D illustrate an example of a process for cyst management utilizing the catheter system 100 described above.

Figure 6A:
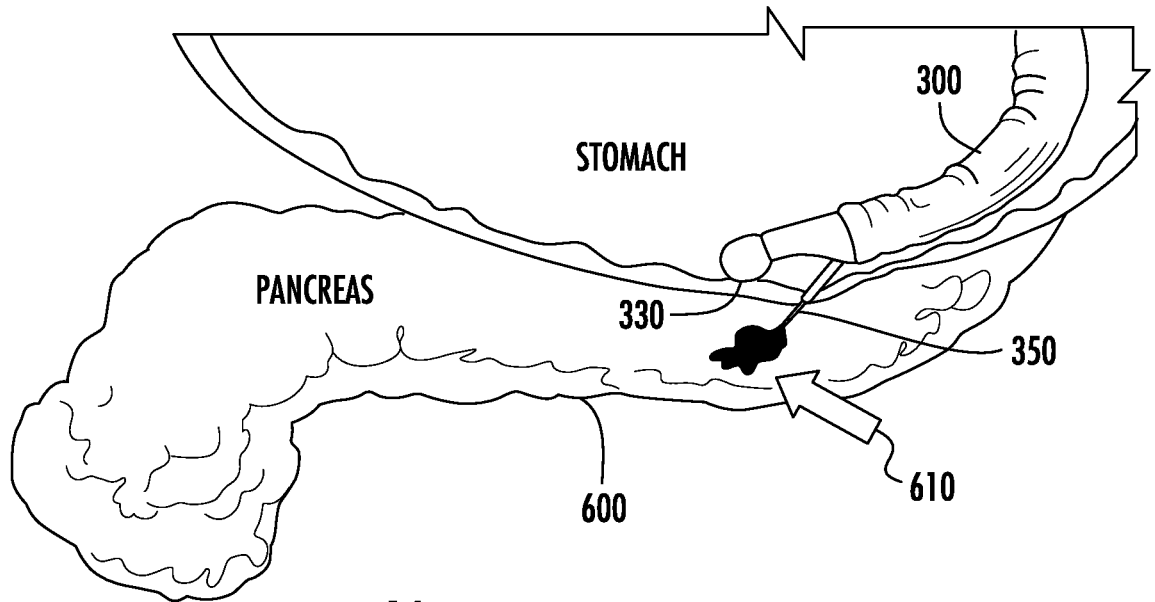
FIGS. 6A-6D illustrate various views of a pancreas having a cyst treatment site, and are used to describe one embodiment of a method for deploying an expandable material using the catheter system of FIG. 1A to treat pancreatic cysts.

In FIG. 6A, the endoscope 300 may be advanced to a target position proximate a cyst 610 in the pancreas 600, for example along a gastrointestinal tract. Visualization of the environment and targeting of the cyst may be facilitated using the ultrasound transducer 330. An aspiration needle 350 may be advanced from the working channel of the endoscope 300 into the cyst 610 to drain cyst fluid.

Figure 6B:
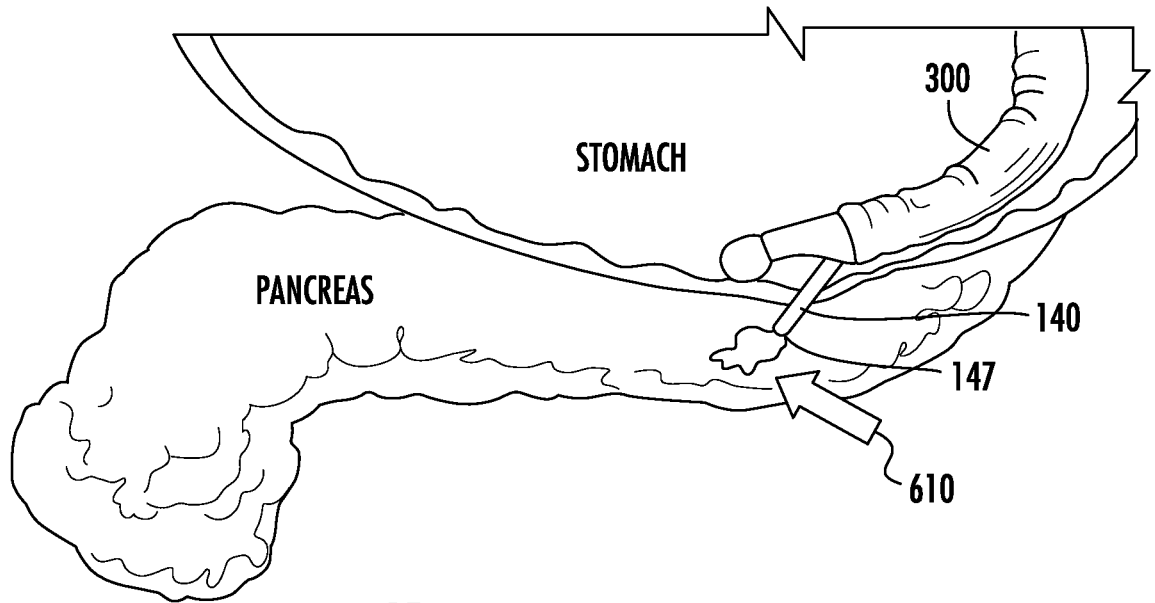

As shown in FIG. 6B, following draining of cyst fluid, in one embodiment the needle is withdrawn and the distal end 147 of the catheter 140 may be advanced through the endoscope 300 towards the cyst 610.

Figure 6C:
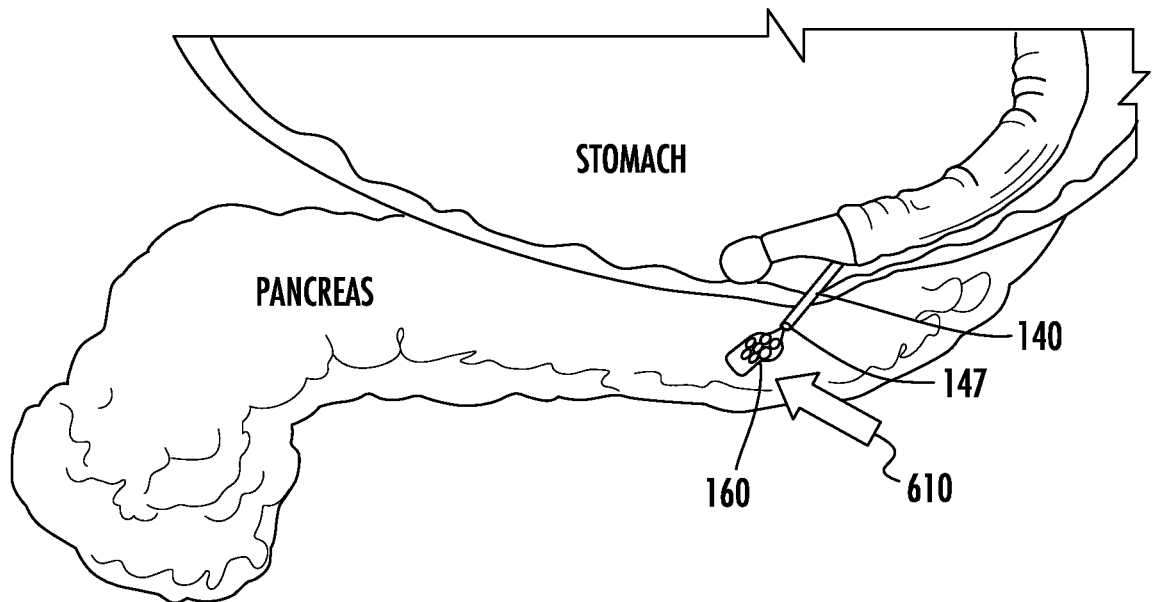

As shown in FIG. 6C, following advancement of the distal end 147 of the catheter 140 to the cyst 610, the foam 160 may be released into the cyst 610. In one embodiment, prior to, during and/or after release of the foam 160 into the cyst 610, a proximal vacuum force draws the walls of the cyst and/or the foam towards the distal end 147 of the catheter 140, reducing the size of the cyst.

Figure 6D:
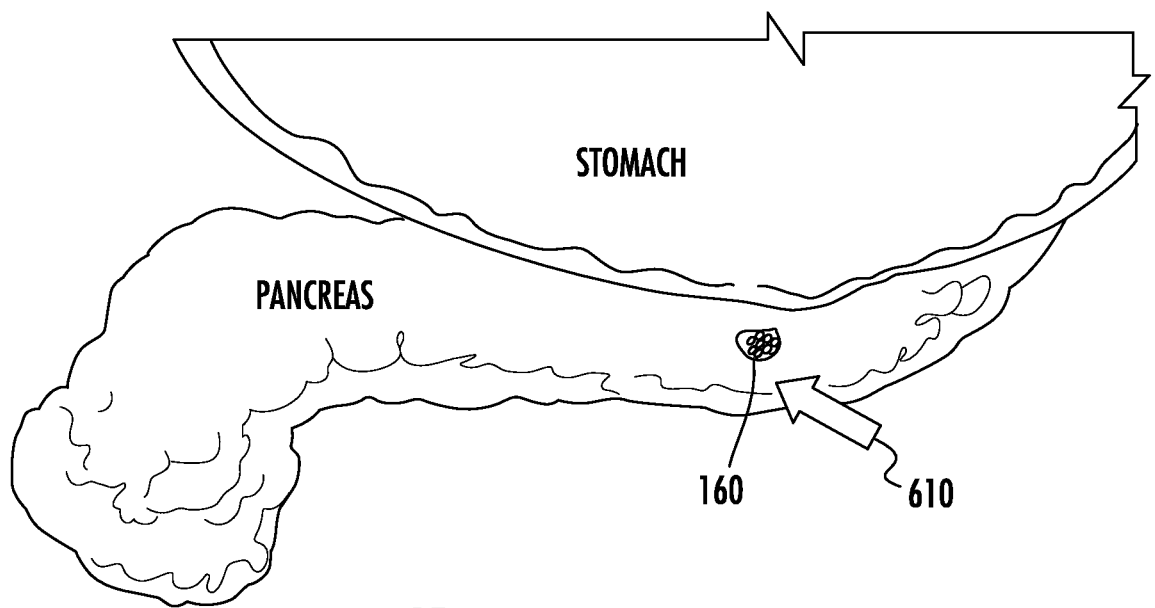

Following administration of the foam, in FIG. 6D, the endoscope may be removed from the gastrointestinal tract, and/or positioned to treat a different cyst. The cyst 610 remains, in reduced form with added foam 160, which continues to absorb cyst fluid over time, reducing cyst recurrence.

It should be noted that although the catheter system and method of use has been described as part of a transluminal procedure, other methods of access, including laparoscopic, percutaneous, and/or using endoscopic retrograde cholangiopancreatography may similarly benefit from the concepts disclosed herein.

Accordingly, catheter system and method of use thereof has been shown and described. Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A device comprising: a catheter, wherein the catheter comprises an elongated body having a proximal end, a distal end, and a lumen extending from the proximal end to the distal end, a sheath disposed about the elongated body, the sheath having a distal tip that extends distally beyond the distal end of the elongated body to form a chamber within the sheath distally of the distal end of the elongated body; an absorbent material disposed within the chamber of the sheath; a handle coupled to a proximal end of the sheath, the handle comprising a release mechanism; a vacuum passage configured to apply a proximal suction force through the lumen; and a push rod coupled to the release mechanism and extending through the lumen, wherein the push rod is configured to release the absorbent material from the chamber, and wherein the push rod forces the absorbent material from the chamber.

2. The device of claim 1, wherein the handle comprises a source of the suction force.

3. The device of claim 1, wherein the handle is coupled to a source of the suction force.

4. The device of claim 1, wherein: the handle includes a housing having a bore extending from a proximal opening of the housing to a distal inlet of the housing, the proximal end of the elongated body fluidly coupled to the distal inlet of the housing; a source of the suction force includes a plunger rod translatably disposed with in the bore, the plunger rod comprising a plunger translatable within the bore; and the plunger rod and the plunger are configured to move proximally through the bore to decrease a pressure within the housing and the lumen of the elongated body to generate the proximal suction force.

5. The device of claim 1, wherein the release mechanism includes one of a knob, a switch, a thumbwheel, a button, a dial, or a combination thereof.

6. The device of claim 1, wherein the absorbent material comprises foam.

7. The device of claim 6, wherein the foam is bioabsorbable.

8. The device of claim 6, wherein the foam includes a radiolucent or echogenic material.

9. The device of claim 6, wherein the foam is a drug eluting foam.

10. The device of claim 1, wherein the catheter of the device is configured for translation through a working channel of an endoscope.

11. The device of claim 1, wherein the catheter is configured for translation through a needle lumen of a needle catheter.

12. The device of claim 1, wherein the push rod extends from a proximal end to a distal end, and wherein the distal end of the push rod is adjacent the chamber and the proximal end of the push rod is adjacent the release mechanism.

13. The device of claim 1, wherein an entirety of the absorbent material, when disposed within the chamber of the sheath, is distal to the lumen.

14. A catheter system comprising: a catheter, wherein the catheter comprises an elongated body having a proximal end, a distal end, and a lumen extending from the proximal end to the distal end, a sheath disposed about the elongated body, the sheath comprising a distal tip that extends distally beyond the distal end of the elongated body to form a chamber distally of the distal end of the elongated body; an absorbent material having a compressed configuration sized to fit within the chamber of the sheath and an expanded configuration larger than the compressed configuration, the absorbent material comprising a radiolucent material, an echogenic material, a drug eluting material, a bioabsorbable material, or a combination thereof; a handle coupled to a proximal end of the sheath, the handle comprising a release mechanism shaped and configured to release the absorbent material from the chamber; a vacuum passage configured to apply a proximal suction force through the lumen; and a push rod coupled to the release mechanism and extending through the lumen, wherein the push rod is configured to release the absorbent material from the chamber, and wherein the push rod forces the absorbent material from the chamber.

15. The catheter system of claim 14, wherein the release mechanism includes one of a knob, a switch, a thumbwheel, a button, a dial, or a combination thereof.

16. The catheter system of claim 14, further comprising: a housing having a bore extending from a proximal opening of the housing to a distal inlet of the housing; wherein: the distal inlet of the housing is fluidly coupled to the proximal end of the elongated body; a source of the suction force includes a plunger rod translatably disposed within the bore of the housing, the plunger rod comprising a plunger translatable within the bore of the housing; and the plunger rod and the plunger are configured to move proximally through the bore of the housing to decrease a pressure within the housing and the lumen to generate the proximal suction force.

17. The catheter system of claim 14, wherein the catheter is configured for translation through a working channel of an endoscope, a lumen of a needle catheter, or both.

18. A device comprising: a catheter, wherein the catheter comprises an elongated body having a proximal end, a distal end, and a lumen extending from the proximal end to the distal end, a sheath disposed about the elongated body, wherein a distal end of the sheath includes a chamber distal to the lumen; an absorbent material disposed within the chamber; a handle coupled to a proximal end of the sheath, the handle comprising a release mechanism configured and positioned to release the absorbent material from the chamber; a vacuum passage configured to apply a proximal suction force through the lumen and to the distal end of the sheath; and a push rod coupled to the release mechanism and extending through the lumen, wherein an entirety of the absorbent material is distal to the push rod.

* * * * *